United States Patent [19]

Kariyone et al.

[11] Patent Number: 5,081,037
[45] Date of Patent: Jan. 14, 1992

[54] ENZYME ELECTRODE FOR MEASURING MALTO-OLIGOSACCHARIDE

[75] Inventors: Akio Kariyone, Kyoto; Yoshio Hashizume, Kakogawa; Ryuzo Hayashi, Higashiosaka, all of Japan

[73] Assignee: Kanzaki Paper Mfg. Co., Ltd., Tokyo, Japan

[21] Appl. No.: 321,165

[22] Filed: Mar. 9, 1989

[30] Foreign Application Priority Data

Mar. 15, 1988 [JP] Japan .................. 63-61322

[51] Int. Cl.$^5$ .................................. C12M 1/40
[52] U.S. Cl. .................. 435/288; 435/175; 435/817; 435/913; 435/939; 204/403
[58] Field of Search ............ 435/288, 175, 177, 817, 435/913, 939; 204/403

[56] References Cited

U.S. PATENT DOCUMENTS

| | | | |
|---|---|---|---|
| 4,172,765 | 10/1979 | Keyes | 435/14 |
| 4,340,448 | 7/1982 | Schiller et al. | 204/1 T |
| 4,810,642 | 3/1989 | Aoyama et al. | 435/28 |

FOREIGN PATENT DOCUMENTS 0145398  6/1985  European Pat. Off. .

OTHER PUBLICATIONS

Inman et al., Biochem. J., 137, 25–32 (1974).
Patent Abstracts of Japan, vol. 10, No. 183 (P-472) [2239], 6/26/86.
Patent Abstracts of Japan, vol. 10, No. 344 (P-518) [2400], 11/20/86.
Pfeiffer et al., Biochimie, No. 62, 1980, pp. 587–593.
Chemical Abstracts, 102: 181456W, 1985.
Walker, J. M. and Cox, M., The Language of Biotechnology A Dictionary of Terms, Maple Press Co., 1988, p. 111.

Primary Examiner—David L. Lacey
Assistant Examiner—J. D. Waack
Attorney, Agent, or Firm—Wenderoth, Lind & Ponack

[57] ABSTRACT

An enzyme electrode for measuring malto-oligosaccharides having a co-immobilized enzyme membrane containing glucoamylase and a glucose oxidizing enzyme such as glucose oxidase or pyranose oxidase.

The glucoamylase and glucose oxidizing enzyme are immobilized at a ratio of $$\frac{Va}{Vo} \geq 0.4$$

where Va is the maximum reaction rate of glucoamylase as expressed in the glucose formation rate from maltose, and Vo is the maximum reaction rate of glucose oxidizing enzyme as expressed in the hydrogen peroxide formation rate from glucose.

In such enzyme electrode, malto-oligosaccharides are detected at the response value proportional to their degree of polymerization. Therefore, the malto-oligosaccharides can be measured at the glucose converted concentration.

4 Claims, 6 Drawing Sheets

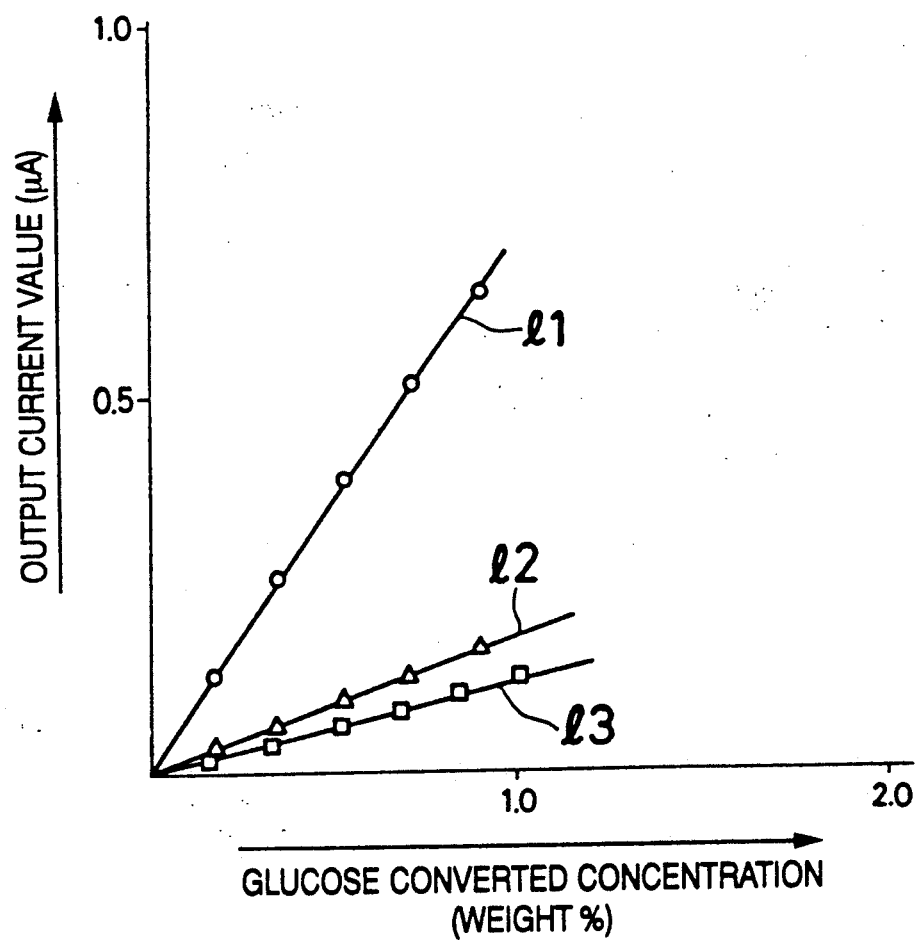

ENZYME ELECTRODE FOR MEASURING MALTO-OLIGOSACCHARIDE

BACKGROUND OF THE INVENTION

1. Field of the Invention

This invention relates to an immobilized enzyme electrode (hereinafter abbreviated enzyme electrode), and more particularly to an enzyme electrode for measuring malto-oligosaccharides, especially malto-oligosaccharides in which the degree of polymerization is different providing an equal response per wt. % concentration of the malto-oligosaccharide for each degree of polymerization and, to a measuring method using the same.

2. Description of the Prior Art

Malto-oligosaccharides are manufactured by acid hydrolysis or enzymolysis of starch. They are not only used as sweeteners or thickening agents in the food processing field, but are also widely applied as materials for pharmaceuticals or is a substrate for measuring alpha-amylase activity in the field of clinical examinations. Accordingly, the development of the method of measuring their concentration is an important issue.

Malto-oligosaccharides are usually analyzed by high performance liquid chromatography because they are water-soluble and hardly volatile compounds. In an HPLC assay, however, the pretreatment is complicated including deionization and deproteinization of the sample, and the analysis takes a long time.

Recent attention therefore has been turned to a method of analysis using an enzyme, in particular, a method using biosensors capable of analysis in a short time with almost no pretreatment and without requiring instruments such as a spectrophotometer. Among the methods of analysis using biosensors, the method most widely employed at the present time and having the highest reliability is the enzyme electrode method which is designed to oxidize or reduce the substrate enzymatically and detect the decrease of oxygen or formation of hydrogen peroxide, etc. as a current value.

At the present time, however, the enzyme capable of oxidizing or reducing the malto-oligosaccharide in one step is not practically usable. Therefore the malto-oligosaccharide is first hydrolyzed to obtain glucose, the formed glucose is then oxidized by glucose oxidase, and the decrease of oxygen or formation of hydrogen peroxide by this reaction is detected electrochemically.

On the other hand, the attempt to measure maltose by using glucoamylase and glucose oxidase is relatively old. For example, Inman et al. (D. J. Inman, W. E. Hornby: Biochem. J., 137, 25–32, 1974) immobilized glucoamylase and glucose oxidase in a nylon tube, and passed a sample containing maltose, in a continuous tube, and determined its concentration.

In the method by Inman et al. spectroscopic means were used in the final detection. Thereafter, with the purpose of detecting maltose, an enzyme electrode immobilizing glucoamylase and glucose oxidase has been studied.

The principle of an enzyme electrode method for measuring malto-oligosaccharides is as follows. In the immobilized enzyme layer on the electrode, the molecule of malto-oligosaccharide is diffused from the sample solution, and is hydrolyzed by glucoamylase as shown in the formula below, and glucose is formed.

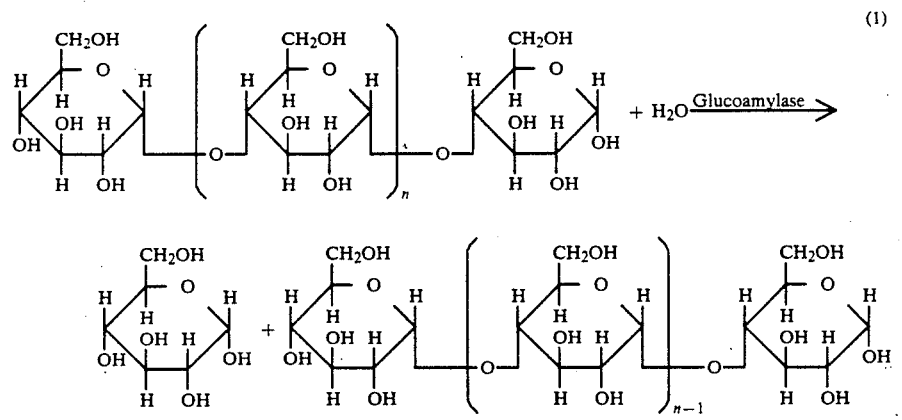

(1)

In formula (1), for the sake of simplicity, the malto-oligosaccharide is expressed in an normal chain, and only a cyclic form of sugar is illustrated. Glucoamylase catalyzes the cleavage of the non-reducing terminated glucose from the malto-oligosaccharide one by one.

Glucose is further oxidized by glucose oxidase, and hydrogen peroxide is formed as shown below.

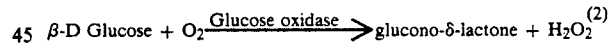

(2)

The generated hydrogen peroxide is oxidized by the platinum electrode, and this electrolytic current is detected as a signal. The generation rate of hydrogen peroxide is proportional to the concentration of the original malto-oligosaccharides. Thus, the concentration of the original malto-oligosaccharides is converted into a current signal and is detected.

Generally speaking, the diffusion rate of the substrate into the enzyme layer on the electrode depends on the substrate consumption rate by enzymatic reaction in the enzyme layer and the substrate concentration in the sample solution. The diffusion rate is determined so that the diffusion rate and the substrate consumption rate may be balanced. Therefore, in the enzyme layer, when the enzyme reaction rate to the unit concentration of substrate is constant, the formation rate of the enzyme reaction product formed in the enzyme layer is proportional to the substrate concentration in the sample solution.

In the clinical field, various research has concentrated on the maltose sensor for measuring alpha-amylase activity. Conventionally, in the examination of pancreatitis or hepatitis, maltopentaose was mixed with a blood sample, and the concentration of maltose in the sample was measured a specific time later. Since the maltopentaose is decomposed by alpha-amylase into, for example, maltose and maltotriose and the reducing power is increased, consequently the state of alpha-amylase activity in blood can be examined. In such an assay, when an approximate value of malto-oligosaccharide is known, the activity of alpha-amylase can be measured. It has not been attempted in the clinical field to measure accurately the malto-oligosaccharides differing in the degree of polymerization.

In actual use, however, malto-oligosaccharides do not have the same degree of polymerization of glucose, but are actually mixtures of various substances such as maltose, maltotriose and maltotetraose. In determining these malto-oligosaccharides, it is often required to measure the total glucose concentration, that is, the wt. % concentration. For example, in the fermentation process of beer or sake, the starch contained in the material is converted into alcohol through malto-oligosaccharide and glucose. In such a fermentation process, in order to measure the degree of fermentation and control the flavor of beer or sake, it is required to measure the concentration of malto-oligosaccharide as converted into glucose concentration.

However, because malto-oligosaccharides differ in the degree of polymerization, they also differ in the enzyme reaction rate by glucoamylase depending on the degree of polymerization. Therefore the apparent glucose converted concentration of malto-oligosaccharide varies depending on the composition of malto-oligosaccharides with various degrees of polymerization in the sample.

The reaction rate theory of glucoamylase is most profoundly studied among amylases. When the chain length of the malto-oligosaccharide varies, both Michaelis constant and molecular activity are changed. This is explained by the subsite theory from the viewpoint of the interaction of the enzyme active center and substrate. When malto-oligosaccharides having various chain lengths (e.g. maltose, maltotriose, maltotetraose) are hydrolyzed by glucoamylase, the rate of hydrolysis for each malto-oligosaccharide differs. When measuring by putting such enzyme and glucose oxidase into the same enzyme layer, it may be possible to determine a monodisperse oligosaccharide having only one type of chain length, but it is difficult to plot a calibration curve in a mixture. No effective analysis method has been presented so far.

SUMMARY OF THE INVENTION

This invention relates to the assay of malto-oligosaccharides using an enzyme electrode manufactured by immobilizing glucoamylase and glucose oxidase.

It is hence a primary object of this invention to present an apparatus for measuring malto-oligosaccharides capable of measuring malto-oligosaccharides differing in the degree of polymerization by increasing the response value to the unit molar number in proportion to the degree of polymerization. Then, the response value to the unit weight percent may be identical in the malto-oligosaccharides with each degree of polymerization. Since malto-oligosaccharides are polymers of glucose and if the mixture is composed of malto-oligosaccharides differing in the degree of polymerization, for example, the glucose converted concentrations are the same as when the weight percentage is identical, regardless of the composition ratio of molecules differing in the degree of polymerization.

In order to achieve the above object, the invention presents an enzyme electrode for measuring malto-oligosaccharides, having an immobilized enzyme membrane containing glucoamylase and glucose oxidase, characterized in that, glucoamylase and glucose oxidase are immobilized so that the ratio Co may be $$Co = \frac{Va}{Vo} \geq 0.4$$

where Va is the maximum reaction rate of glucoamylase as expressed in the glucose formation rate from maltose and Vo is the maximum reaction rate of glucose oxidase as expressed in the hydrogen peroxide formation rate from glucose.

Conventionally, in the enzyme electrode for measuring mainly maltose, the ratio of activity of glucoamylase and glucose oxidase was not usually adjusted accurately. Whether adjusted or not, in the conventional enzyme electrode, the ratio was less than 0.4 times the maximum reaction rate of this invention.

The present inventors discovered a surprising fact that the output values per unit wt. % concentration of malto-oligosaccharides become identical by using an enzyme electrode having the glucoamylase and glucose oxidase immobilized so that the ratio Co of the maximum reaction rate Va of glucoamylase as expressed in the glucose formation rate from maltose to the maximum reaction rate Vo of glucose oxidase as expressed in the hydrogen peroxide formation rate from glucose may be 0.4 or more, and thereby reached the completion of this invention.

The outline of the method of determining the maximum reaction rate in the catalyst activity of enzyme is described below. Generally, the quantity of enzyme is not sufficiently known by expressing only the weight and protein concentration, and more practically it must be expressed by the catalyst activity of enzyme.

The reaction rate V of catalyst reaction by enzyme is expressed in formula (3).

$$V = \frac{Vm \cdot S}{Km + S} \quad (3)$$

where Vm is the maximum reaction rate, Km is the Michaelis constant, and S is the substrate concentration.

It is known from reaction rate theory that Vm is related to both enzyme concentration and its catalytic activity. Therefore, it is reasonable to use Vm as a practical index for enzyme amount.

Samples composed of plural different substrate concentrations S are caused to act on an enzyme of specified concentration, and the decrease of substrate or increase of product is measured at specified time intervals. When the change of the substrate is sufficiently small as compared with the total substrate amount, the changes in the amount measured at specified time intervals will present a linear variation. Accordingly, the amount of change per unit time is calculated to obtain V. In order to determine Vm from a group of S and V values, formula (3) is rewritten as in (4), and the solution may be obtained from the graph.

$$\frac{1}{V} = \frac{1}{Vm} + \frac{Km}{S} \quad (4)$$

That is, the measured values are plotted on a graph, recording 1/S on the axis of abscissas and 1/V on the axis of ordinates, and Vm is calculated from the intersection of the obtained line and the axis of ordinates.

Furthermore, in formula (3), it is also possible to obtain Vm and Km simultaneously by applying the nonlinear method of least squares from a group of S and V values.

By varying the concentration ratio of glucoamylase and glucose oxidase in enzyme electrode, various malto-oligosaccharide aqueous solutions ranging from maltose to maltoheptaose are caused to contact the electrode. The current value per unit concentration (per weight percentage) is determined from the graph of current versus concentration of malto-oligosaccharides, and the results are shown in Table 1. In this table, in order to standardize the output values, the value of each electrode to maltose value is set as 100.

TABLE 1

| | Glucoamylase/glucose oxidase ratio (Co) | | | | | | | | |
|---|---|---|---|---|---|---|---|---|---|
| | 0.15 | 0.30 | 0.40 | 0.80 | 1.00 | 2.00 | 4.00 | 6.00 | 10.00 |
| Maltose | 100 | 100 | 100 | 100 | 100 | 100 | 100 | 100 | 100 |
| Maltotriose | 160 | 150 | 110 | 106 | 103 | 103 | 102 | 101 | 102 |
| Maltotetraose | 200 | 170 | 115 | 112 | 104 | 102 | 103 | 101 | 98 |
| Maltopentaose | 200 | 180 | 120 | 112 | 99 | 100 | 100 | 99 | 98 |
| Maltohexaose | 190 | 185 | 117 | 106 | 103 | 101 | 100 | 100 | 99 |
| Maltoheptaose | 170 | 180 | 115 | 100 | 99 | 99 | 100 | 100 | 99 |

As shown in Table 1, when the maximum reaction rate Va of glucose formation of glucoamylase from maltose is less than 0.4 times the maximum reaction rate Vo of hydrogen peroxide formation of glucose oxidase from glucose, the output value per unit weight percentage differs about two times at maximum with respect to each malto-oligosaccharide, and it is required to plot calibration curves every time when measuring single malto-oligosaccharide. By contrast, at 0.4 times or more, on the basis of maltose, the response value to each malto-oligosaccharide becomes very close to each other. In particular, at a ratio of 1.0 or more, the responses are nearly equal perfectly, and when calibrating the electrode by maltose, the weight percent concentration of other malto-oligosaccharides may be easily calculated. Even in a mixture, the weight percentage can be calculated. However, if the ratio Co exceeds 12 times, the absolute value of the glucose oxidase decreases too much, and the sensitivity is extremely lowered. Therefore, the preferred ratio of the maximum reaction rates of two enzymes should be in a range of 0.4 times to 12 times, or more preferably from 1 to 10 times.

The reason why such characteristics are obtained is not clear, but may be estimated as follows. Generally, in an enzyme electrode immobilizing enzyme according to the reaction rate curve of Michaelis-Menten type, when the substrate concentration in the immobilized enzyme layer is sufficiently low as compared with Michaelis constant (Km), the substrate concentration and reaction rate are in a linear relation. In other words, the substrate concentration and output value are exactly proportional to each other. Likewise, when a malto-oligosaccharide is hydrolyzed by the immobilized glucoamylase, if the substrate concentration is sufficiently lower than Km, the glucose formation rate is proportional to the concentration of malto-oligosaccharide in the layer. However, the glucoamylase varies in Km and molecular activity (kc) depending on the degree of polymerization of malto-oligosaccharide.

By using this value, when the hydrolysis rate (glucose formation rate) of each malto-oligosaccharide to the molar concentration is calculated in the condition that the enzyme concentration is low in the solution, irregular changes are noted if the substrate concentration is relatively high. That is, the rate increases about 7 times from maltose to maltopentaose, and once decreases at maltohexose, and rises again at maltoheptaose. On the other hand, in the immobilized enzyme layer, the relative enzyme amount is very high, while the substrate amount is relatively low because its diffusion is controlled, and it is subjected to a first hydrolysis at an extremely high rate, and glucose and malto-oligosaccharide having one chain length shorter are produced. When calculated similarly in this condition, although there is a certain curvature inclination from maltose to maltoheptaose, the rate of glucose formation ascends nearly in proportion to the chain length. In the immobilized enzyme layer, the formed glucose is quickly oxidized by glucose oxidase to generate hydrogen peroxide, which is detected. If the reaction rate of glucoamylase is sufficiently fast as compared with that of glucose oxidase, the rate-determining step of the entire system becomes the reaction step by glucose oxidase, and the Km of glucose oxidase becomes generally 10 times greater than Km of glucoamylase. Therefore when glucose is produced in proportion to the concentration of the malto-oligosaccharide, hydrogen peroxide is produced in proportion to the glucose amount by the glucose oxidase. To the contrary, when the activity of glucose oxidase is very high, the rate-determining step becomes the glucoamylase reaction, and the entire electrode output value may be considered to show complicated behavior with respect to the chain length intrinisc to the glucoamylase.

Incidentally, glucose exists, in a solution, as a mixture of about 60% of beta-anomer and about 40% of alpha-anomer. Glucose oxidase oxidizes only beta-anomer among them. On the other hand, glucoamylase releases glucose from malto-oligosaccharide in the form of beta-anomer. In the immobilized enzyme layer, the released beta-anomer is quickly oxidized before it is changed into alpha-beta mixture by the mutarotation phenomenon. When the activity of glucoamylase is measured in a solution system based on maltose, since the mutarotation is sufficiently advanced, the formation rate of the mixed glucose of alpha- and beta-anomers is obtained. Therefore, when glucoamylase and glucose oxidase are immobilized with the ratio Va/Vo of the maximum reaction rates in the solution set at 0.4, when maltose is hydrolyzed in the immobilized enzyme electrode, the substrate of glucose oxidase (glucose) is not formed at a rate of 0.4×2, but since 60% of the reducing ends of maltose are beta-anomers and 100% of glucose cut from non-reducing terminal of malto-oligosaccharide is beta-anomers, the rate of 0.4+(0.4/0.6), that is, the beta-glucose formation rate of about 1.1 times the glucose consumption rate of glucose oxidase is obtained, and it is considered that the reaction by glucose oxidase becomes the rate-determining step of the entire system.

In the malto-oligosaccharide having a longer chain length, the reaction by glucose oxidase becomes the rate-determining step, and apparently the output value per unit molar number to the malto-oligosaccharide is proportional to the chain length, and it is considered that the output values per unit wt. % concentration be identical. Therefore, in order to set the reaction by glucose oxidase as the rate-determining step reaction, it is enough, as mentioned above, to set the reaction rate by glucoamylase at 0.4 times or more that by glucose oxidase.

Meanwhile, if the activity of glucoamylase is extremely large compared with that of glucose oxidase, the glucose oxidase amount decreases and the output decreases when the glucoamylase protein is constant, or the protein of glucoamylase increases and the membrane becomes thick to retard the reaction rate when the glucose oxidase amount is constant. It is therefore not preferable to increase the maximum reaction rate ratio Co too much.

As for glucoamylase, many enzyme specimens are obtained from mold fungi such as Rhizopus, Aspergillus and Mucor, and bacteria such as Bacillus, and all of them can be used in this invention. In consideration of the pH, temperature and other conditions simultaneously optimal for glucose oxidase which is immobilized at the same time, and also in order to obtain enzyme electrodes of longer life, enzymes derived from Rhizopus and Aspergillus are preferred.

That is, glucose oxidase has the optimal pH in the vicinity of the neutral point (pH 6 to 7), and glucoamylases derived from Rhizopus and Aspergillus have their optimal pH range near the optimal pH range of glucose oxidase. When the buffer solution in which the sample is injected is set at this pH range, the sensitivity of the enzyme electrode is superbly enhanced.

Also as glucose oxidase, enzymes derived from Aspergillus or Pencillium may be used.

Furthermore, as for glucose oxidizing enzyme, the same results will be obtained by using pyranose oxidase derived from Basidiomycetae, instead of glucose oxidase.

That is, the enzyme electrode used in this invention is characterized in, glucoamylase and pyranose oxidase are immobilized so that the ratio Cp may be $$Cp = \frac{Va}{Vp} \geq 0.4$$

where Va is the maximum reaction rate of glucoamylase as expressed in the glucose formation rate from maltose and Vp is the maximum reaction rate of pyranose oxidase as expressed in the hydrogen peroxide formation rate from glucose.

Thus, also when pyranose oxidase is used, since the optimal pH range of this pyranose oxidase is similarly pH 6 to 7, it is desired that glucoamylase be derived from Rhizopus or Aspergillus.

Another feature of the invention is that glucoamylase and glucose oxidase are preferably immobilized by crosslinked using a multifunctional reagent, and formed into a membrane form.

In this invention, various enzyme immobilizing methods may be employed, such as entrapping method, ion exchanger bonding method and other covalent bonding method. However, in order to make uniform the concentration ratio of enzyme and measure stably, it is desired to crosslink the enzyme by using protein such as bovine serum albumin and multifunctional reagent such as glutaraldehyde, and immobilize by forming in a membrane from.

Moreover, in order to eliminate electrochemical obstacles for actual analysis of samples, such as ascorbic acid, uric acid and reducing glutathione when detecting hydrogen peroxide, a permselective membrane may be installed between the immobilized enzyme layer and the electrode (for example platinum plate).

As understood from the description above, malto-oligosaccharides are supplied as mixtures of polysaccharides having various degrees of glucose polymerization, and the practically required concentration indication is the glucose converted concentration or wt. %. In the conventional enzyme electrode method, since the output differs depending on the composition ratio of malto-oligosaccharides, the calibration curve must be plotted every time for each different composition rate, and this was very troublesome. By contrast, in this invention, once a calibration curve is made for maltose, malto-oligosaccharides of any composition ratio can be measured thereafter, and the measuring efficiency is notably enhanced.

Moreover, this invention presents a measuring apparatus for glucose and malto-oligosaccharides comprising;

means for continuously supplying a buffer solution at a predetermined flow rate, means for injecting a sample solution into the buffer solution from the supplying means, a first enzyme electrode, installed at the downstream side of the injection means, having an immobilized glucose oxidase membrane, and for detecting glucose, and a second enzyme electrode having an immobilized glucose oxidase and glucoamylase membrane, and for detecting glucose and malto-oligosaccharides, in which the glucoamylase and glucose oxidase of the second enzyme electrode are immobilized at a ratio Co of $$Co = \frac{Va}{Vo} \geq 0.4$$

where Va is the maximum reaction rate of glucoamylase as expressed in the glucose formation rate from maltose, and Vo is the maximum reaction rate of glucose oxidase as expressed in the hydrogen peroxide formation rate from glucose. In such a case, too, as the glucose oxidizing enzyme, pyranose oxidase can be used instead of glucose oxidase.

In this way, the first enzyme electrode having an immobilized glucose oxidase or pyranose oxidase membrane, and the second enzyme electrode having an immobilized glucose oxidase or pyranose oxidase and glucoamylase membrane are provided.

In such flow type measuring apparatus comprising two enzyme electrodes, the accurate concentration of malto-oligosaccharide can be determined by subtracting the portion contributed by the glucose calculated by the glucose output value detected by the first enzyme electrode from the output value of glucose and malto-oligosaccharide detected by the second enzyme electrode.

Consequently glucose and malto-oligosaccharide can be measured at the same time.

Still more preferably, the second enzyme electrode is installed at the downstream side of the first enzyme electrode with respect to the flow of the buffer solution from the supplying means, and a tube for diluting the sample solution is installed between the first enzyme electrode and the second enzyme electrode. In such constitution, in the second enzyme electrode, the glucose in the sample solution and the glucose formed by hydrolysis from malto-oligosaccharide are detected, but since the sample solution is diluted in the tube for dilution, if a sample solution of high concentration is measured, the concentration of malto-oligosaccharide can be correctly measured by the second enzyme electrode. Therefore, two substances, that is, glucose and malto-oligosaccharide may be measured in a wide range of concentrations.

BRIEF DESCRIPTION OF THE DRAWINGS

These and other objects of the invention, along with the features and advantages thereof, will be better understood and appreciated from the following detailed description taken in conjunction with the drawings, in which:

FIG. 9 is a graph showing the calibration curve of glucose and maltose in Example 3.

DETAILED DESCRIPTION OF THE PREFERRED EMBODIMENTS

Figure 1:
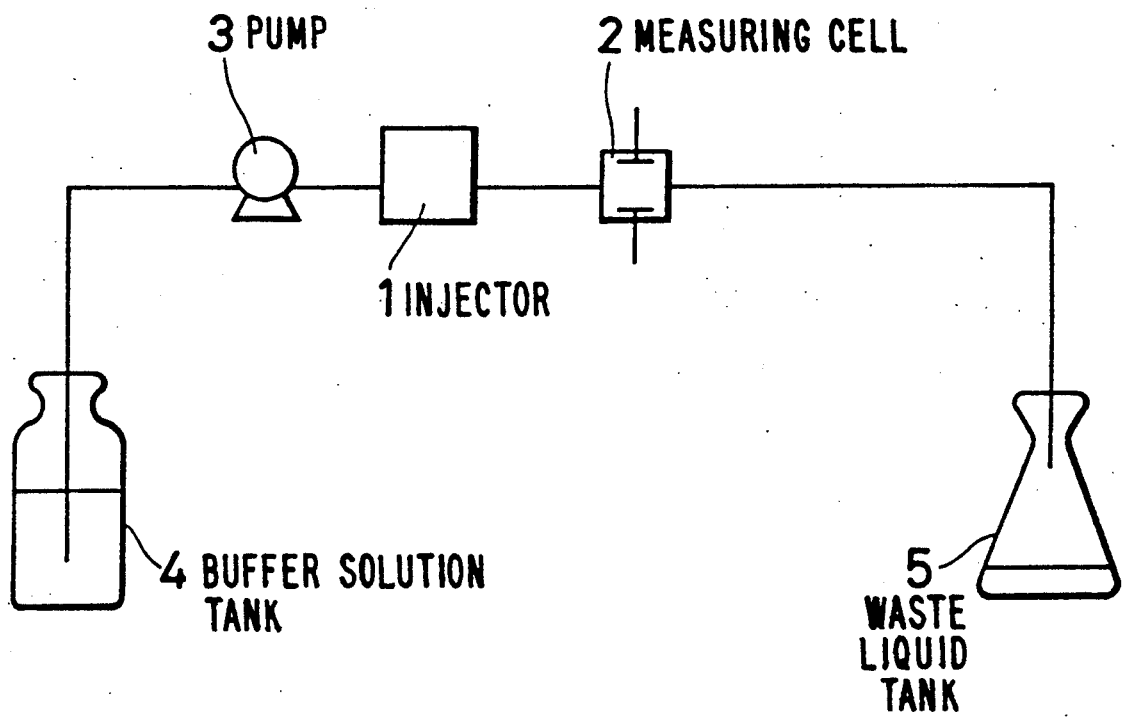
FIG. 1 is a block diagram of a measuring apparatus using an enzyme electrode according to the invention.

Referring now to the drawings, preferred embodiments of the invention are described in detail below.

EXAMPLE 1

1 mg of glucose oxidase (manufactured by Sigma, type II, Lot No. 75-9595), 16.7 $\mu$l of glucoamylase (manufactured by Sigma, Lot No. 46F-05572), and 5 mg of bovine serum albumin (manufactured by Sigma, fraction V, Lot No. 45F-0064) were dissolved in 100 mM phosphate buffer at pH 6.0 containing 0.2 wt. % of glutaraldehyde to make up 1000 $\mu$l in total. This mixed enzyme solution contains an enzyme amount indicating a maximum reaction rate of 16 $\mu$mol/min, at the maximum reaction rate Vo expressing glucose oxidase in the hydrogen peroxide formation rate. Moreover, at the maximum reaction rate Va expressing glucoamylase in the glucose formation rate from maltose, it contains an enzyme amount indicating a maximum reaction rate of 10 $\mu$mol/min, and hence the maximum reaction rate ratio Co of glucoamylase to glucose oxidase is 0.62.

This mixed enzyme solution was dropped by 5 $\mu$l on the surface of a platinum electrode of 2 mm in diameter and developed, and immobilized for 30 minutes at 40° C., and an enzyme electrode was obtained. As the measuring apparatus (FIG. 1), an injector 1 for HPLC capable of injecting sample in the $\mu$l order, and a measuring cell 2 mounted with the enzyme electrode were connected together by using a Teflon tube of 0.5 mm in inside diameter.

The inner volume of the measuring cell 2 was 40 $\mu$l, and a reference electrode of Ag/AgCl was disposed opposite to the enzyme electrode, and a voltage of +0.45V to the Ag/AgCl reference electrode was applied to the enzyme electrode, and its current was measured. To feed the buffer solution, a pump 3 for HPLC was used, 100 mM phosphate buffer solution at pH 6.0 was fed at a flow rate of 1.0 ml/min from a Buffer solution tank 4. The solution from the measuring cell 2 is discharged into a waste liquid tank.

Figure 2:
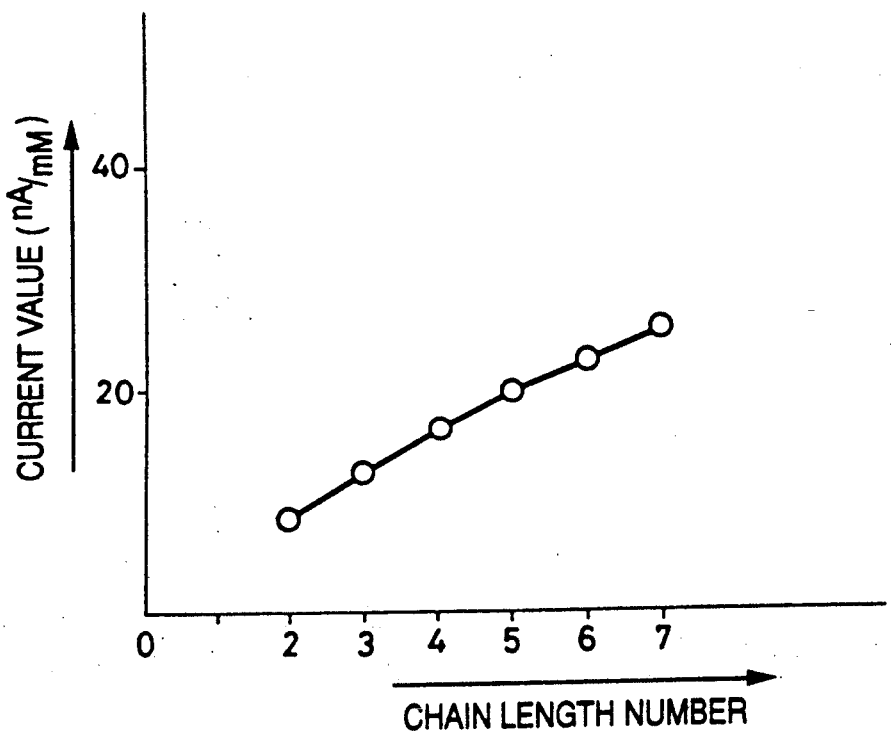
FIG. 2 is a graph showing the results of measurement by using the enzyme electrode in Example 1.
Figure 3:
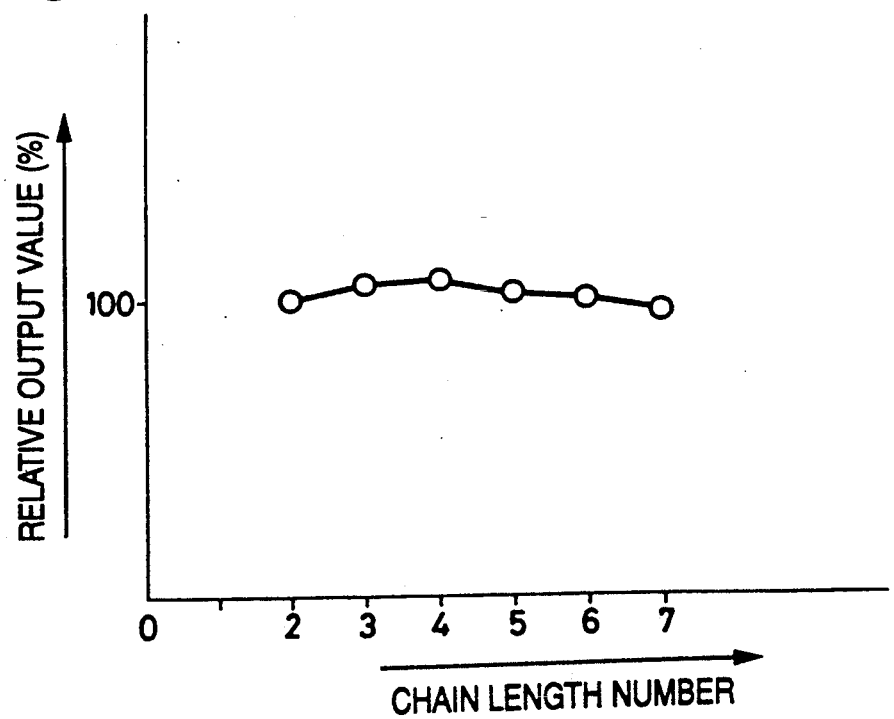
FIG. 3 is a graph showing the relation between the degree of polymerization of malto-oligosaccharide and the relative output value in Example 1.

A concentration series was prepared by using aqueous solutions of maltose, maltotriose, maltotetraose, maltopentaose, maltohexaose and maltoheptaose, and a calibration curve of each substance was plotted. When the inclination of this calibration curve, that is, the relation between the output value per unit molar concentration of each substance and the chain length number (degree of polymerization) of sugar chain of malto-oligosaccharide was studied, a proportional relation with chain length number of sugar chain was found as shown in FIG. 2. Besides, when the relation between the output value per unit wt. % concentration of each substance and the chain length number of sugar chain of malto-oligosaccharide was studied, it was constant regardless of the chain length number of sugar chain of malto-oligosaccharide as shown in FIG. 3.

EXAMPLE 2

Figure 4:
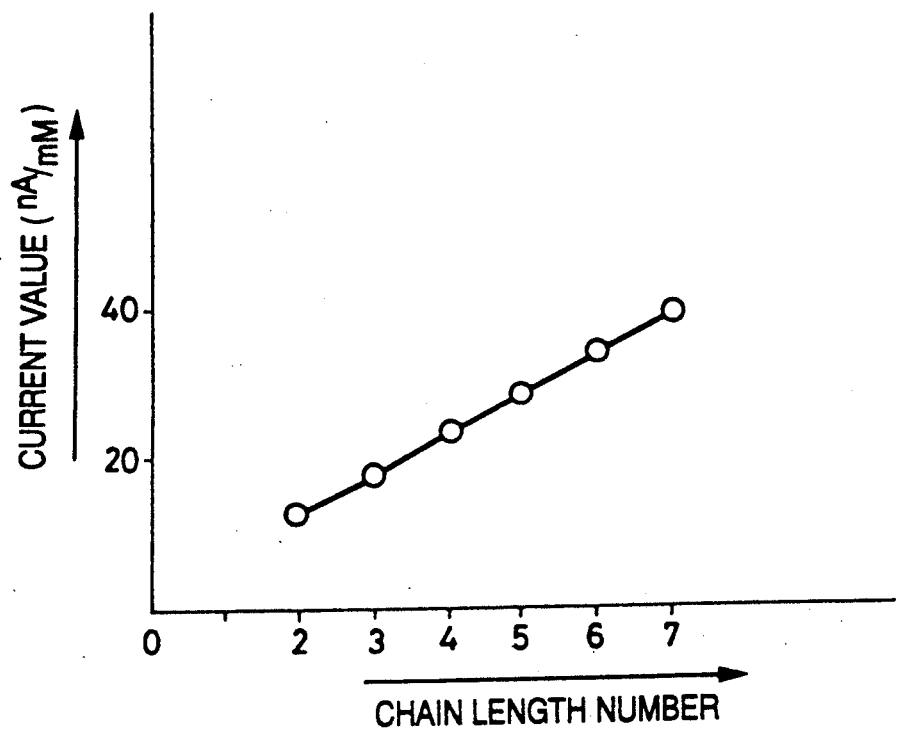
FIG. 4 is a graph showing the results of measurement by using the enzyme electrode in Example 2.
Figure 5:
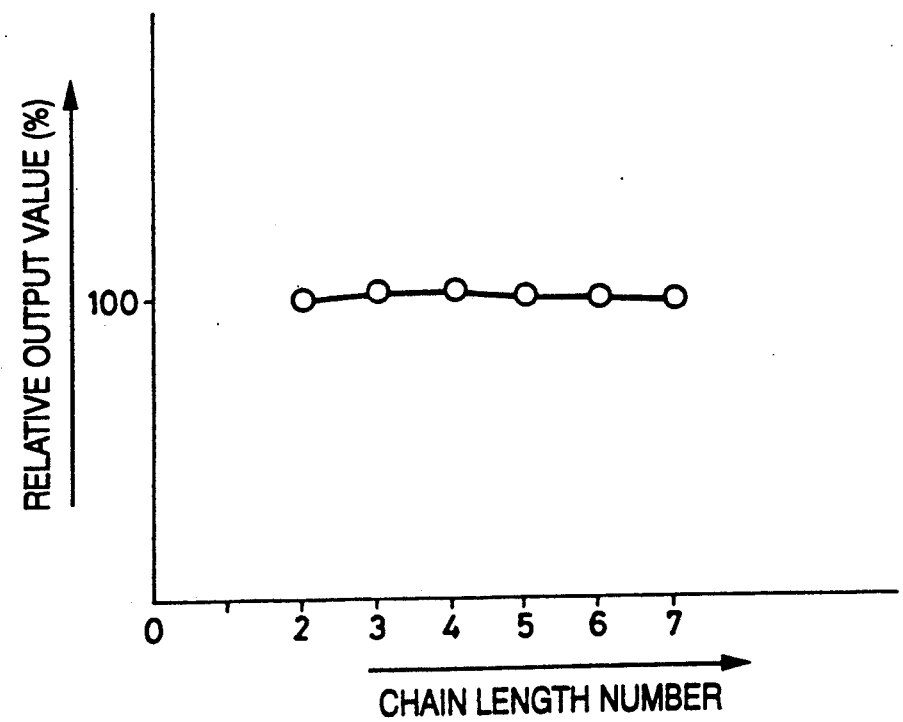
FIG. 5 is a graph showing the relation between the degree of polymerization of malto-oligosaccharide and the relative output value in Example 2.

1 mg of glucose oxidase, 83.4 $\mu$l of glucoamylase, and 5 mg of bovine serum albumin were dissolved in 100 mM phosphate buffer solution at pH 6.0 containing 0.2 wt. % glutaraldehyde to make up 1000 $\mu$l in total. This mixed enzyme solution contains an enzyme amount indicating a maximum reaction rate of 16 $\mu$mol/min, at the maximum reaction rate expressing glucose oxidase in the hydrogen peroxide formation rate. Moreover, at the maximum reaction rate expressing glucoamylase in the glucose formation rate from maltose, it contains an enzyme amount indicating a maximum reaction rate of 50 $\mu$mol/min, and therefore the maximum reaction rate ratio of glucoamylase to glucose oxidase is 3.1. Using this mixed enzyme solution, an enzyme electrode was obtained in the same method as in Example 1. Using the same apparatus as in Example 1, a concentration series was prepared by using aqueous solutions of maltose, maltotriose, maltotetraose, maltopentaose, maltohexaose and maltoheptaose, and a calibration curve of each substance was plotted. When the inclination of this calibration curve, that is, the relation between the output value per unit molar concentration of each substance and the chain length number of sugar chain of malto-oligosaccharide was studied, a proportional relation with chain length number of sugar chain was found as shown in FIG. 4. Besides, when the relation between the output value per unit wt. % concentration of each substance and the chain length number of sugar chain of malto-oligosaccharide was studied, it was perfectly constant regardless of the chain length number of sugar chain of malto-oligosaccharide as shown in FIG. 5.

COMPARATIVE EXAMPLE 1

Figure 6:
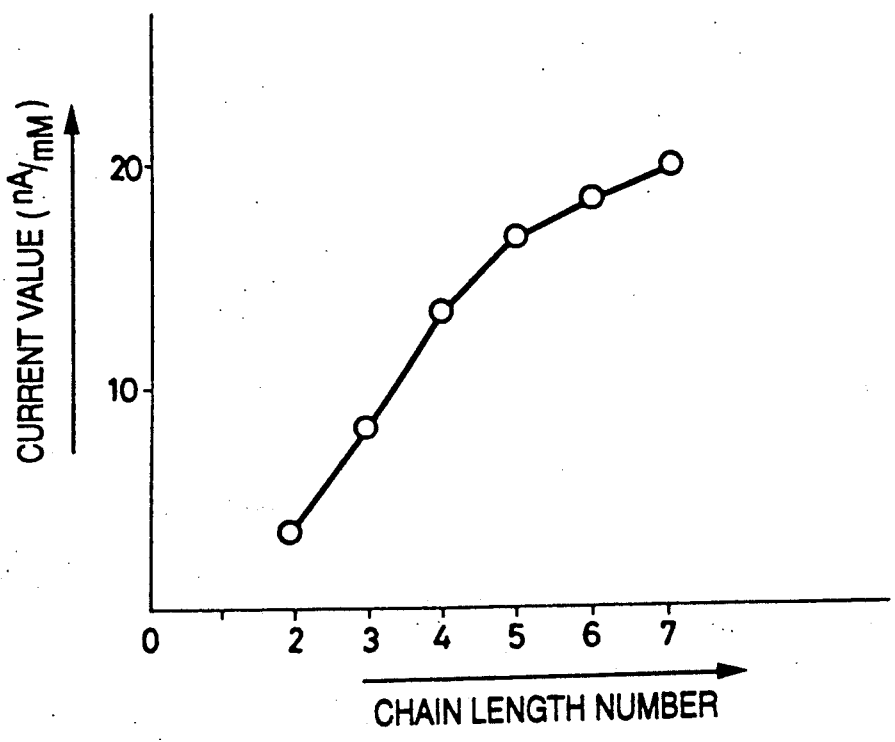
FIG. 6 is a graph showing the results of measurement in Comparative example 1.
Figure 7:
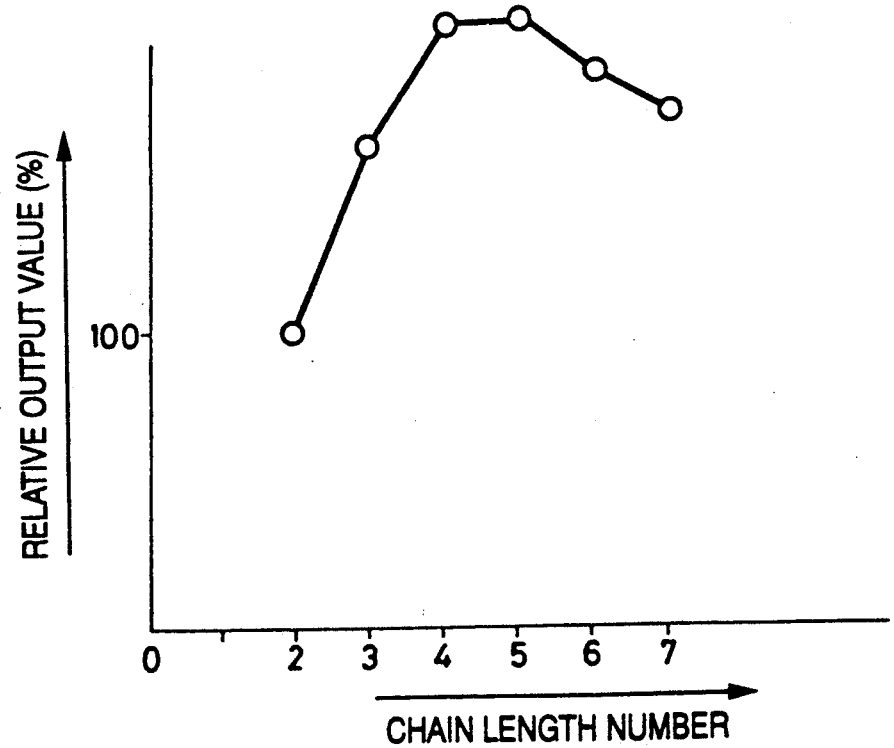
FIG. 7 is a graph showing the relation between the degree of polymerization of malto-oligosaccharide and the relative output value in Comparative example 1.

1 mg of glucose oxidase, 4.0 μl of glucoamylase, and 5 ml of bovine serum albumin were dissolved in 100 mM phosphate buffer solution at pH 6.0 containing 0.2 wt. % of glutaraldehyde to make up 1000 μl in total. This mixed enzyme solution contains an enzyme amount indicating a maximum reaction rate of 16 μmol/min, at the maximum reaction rate expressing glucose oxidase in the hydrogen peroxide formation rate. Moreover, at the maximum reaction rate expressing glucoamylase in the glucose formation rate from maltose, it also contains an enzyme amount indicating a maximum reaction rate of 2.4 μmol/min, and therefore the maximum reaction rate ratio of glucoamylase to glucose oxidase is 0.15. Using this mixed enzyme solution, an enzyme electrode was obtained in the same manner as in Example 1. Using the same apparatus as in Example 1, a concentration series was prepared by using aqueous solutions of maltose, maltotriose, maltotetraose, maltopentaose, maltohexaose and maltoheptaose, and a calibration curve of each substance was plotted. When the inclination of this calibration curve, that is, the relation between the output value per unit molar concentration of each substance and the chain length number of sugar chain of malto-oligosaccharide was studied, any relation proportional to the chain length number was not observed as shown in FIG. 6. Incidentally, the output value per unit wt. % concentration of each substance presented different values for malto-oligosaccharides having different chain lengths as shown in FIG. 7.

EXAMPLE 3

Using a commercial thick malt syrup as the object of analysis, glucose and malto-oligosaccharides in the syrup were measured simultaneously.

Measuring apparatus

Figure 8:
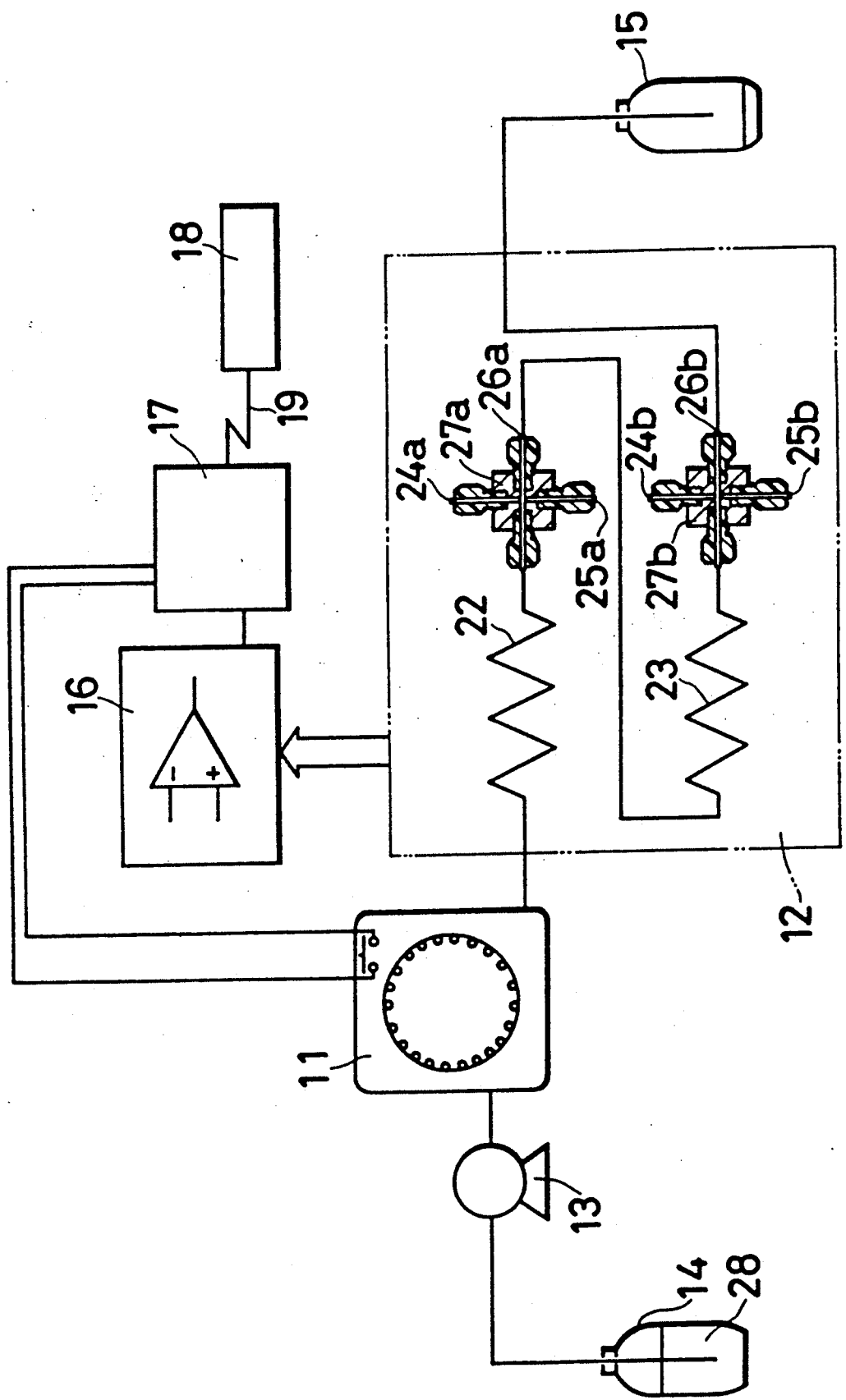
FIG. 8 is a block diagram of a measuring apparatus used in Example 3.

FIG. 8 is a block diagram of a measuring apparatus used in Example 3. Referring to FIG. 8, a buffer solution 28 stored in a buffer solution tank 14 is sent out at a specific flow rate by a pump 13. The buffer solution 28 from a pump 13 is fed into a measuring cell 27a by way of auto-sampler 11 and a tube 22.

In this measuring cell 27a, a first enzyme electrode 24a and a reference electrode 25a are disposed opposedly. The stainless steel tube attached to the measuring cell 27a is used as a counter electrode 26a.

At the downstream side of the measuring cell 27a, another measuring cell 27b is connected by way of a tube 23 for diluting the sample solution. This tube 23 is provided in order to dilute the glucose and malto-oligosaccharides contained in the sample solution by properly diffusing in the axial direction of the tube 23, so that the concentration may be measured correctly by a second enzyme electrode 24b mentioned later even in the case that the sample solution may be comparatively high in the concentration of glucose and malto-oligosaccharides In the measuring cell 27b, similar to the case of the foregoing measuring cell 27a, the second enzyme electrode 24b, reference electrode 25b, and counter electrode 26b are installed. The second enzyme electrode 24b is manufactured as mentioned hereinafter, and glucose oxidase and glucoamylase are immobilized.

The buffer solution containing the sample solution from the measuring cell 27b is discharged into a waste bottle 15.

This auto-sampler 11 can inject 5 μl of sample solution at an interval of 1 minute into the buffer solution pumped out by the pump 13.

The tubes 22, 23 are made of synthetic resin such as Teflon and poly vinyl chloride, or metal such as stainless steel, and in this embodiment, a Teflon tube with the inside diameter of 0.5 mm is used, and its length is 1.5 m in the tube 22 and 1.0 m in the tube 23.

The tube 22, 23, and measuring cells 27a, 27b are disposed in a thermostat 12, and are maintained at a constant temperature, e.g. 37° C.

The outputs of the enzyme electrodes 24a, 24b and reference electrodes 25a, 25b are applied to a potentiometer 16, in which they are converted into voltages. The voltage values may be recorded by a recorder (not shown), or in this embodiment they are applied into a signal processing circuit 17. The signal processing circuit 17 comprises an analog/digital converter, and the measured value converted into a digital value is given to a computer 18 through a line 19. By the computer, the concentrations of glucose and malto-oligosaccharides are calculated from the peak height of the measured values.

Fabrication of second enzyme electrode 24b

The same glucose oxidase and bovine serum albumin as used in Example 1 were used. 15 mg of glucoamlylase (manufactured by Sigma, Lot No. 124F-0369, derived from Rhizopus), 1 mg of glucose oxidase, and 5 mg of bovine serum albumin were dissolved in 100 mM phosphate buffer solution at pH 6.0 containing 0.2 wt. % glutaraldehyde to make up 1000 μl in total. In this mixed enzyme solution, the ratio of maximum rate of reaction of glucose oxidase and glucoamylase is 4.8.

This mixed enzyme solution was dropped by 5 μl on the surface of a platinum electrode of 2 mm in diameter and developed, and immobilized for 30 minutes at 40° C., and an enzyme electrode 24b was obtained.

Fabrication of first enzyme electrode 24a

On the other hand, 1 mg of glucose oxidase and 1 mg of bovine serum albumin were dissolved in 100 mM phosphate buffer at pH 6.0 containing 0.2 wt. % of glutaraldehyde to make up 500 ||1 in total. This mixed enzyme solution was dropped by 5 μl on the surface of a platinum electrode of 2 mm in diameter and developed, and was immobilized for 15 minutes at 40° C., and an enzyme electrode 24a was obtained.

These two electrodes 24a, 24b were installed in the measuring apparatus shown in FIG. 8. The enzyme electrode 24a having only glucose oxidase immobilized was placed at the upstream side, and the enzyme electrode 24b having glucose oxidase and glucoamylase immobilized was placed at the downstream side, across the diluting tube 23 of 0.5 mm in inside diameter and 1.0 m in length.

Plotting of calibration curve

In this apparatus, glucose and maltose solutions were injected, and its sensitivity was calibrated.

The calibration curve plotted at this time is shown in FIG. 9. Line 11 indicates the glucose calibration curve in the first enzyme electrode 24a, and line 12 shows the maltose calibration curve in the second enzyme electrode 24b, and line ⊕ denotes the glucose calibration curve in the second enzyme electrode 24b.

Measurement

Next, the thick malt syrup diluted solution was injected, and the concentrations of glucose and malto-oligosaccharides were determined. As a result, the glucose in the stock solution was 24.8 wt. %, and the malto-oligosaccharides was 46.8 wt. %, which totaled to 71.6 wt. %. Measurement of actual sample terminates in 1 minute if the calibration is complete.

This malto-oligosaccharide electrode maintained the initial sensitivity for more than 6 months when stored at room temperature, and its life is extremely long.

COMPARATIVE EXAMPLE 2

By precisely weighing 5 g of thick malt syrup used in Example 3, it was dried at 105° C. for 10 hours, and the absolute dry weight % was obtained. The result was 71.8 wt. %., which coincided very well with the value determined in Example 3.

This syrup was then diluted 100 times, and was analyzed by HPLC. Water was used as eluate, and the flow rate was kept constant at 0.5 ml/min. The column was a Toso-G-Oligo-PWXL (25 cm length column), and the column temperature was 40° C. By injecting 50 µl of sample, the peak was detected by means of differential refractometer. The syrup contained malto-oligosaccharides mixed with the degree of polymerization of nearly up to 20, and the peak was not separated completely except for glucose. Accordingly, only glucose was determined by using a standard product. Besides, since the differential refractometer shows nearly constant value in the relation between weight concentrations and peak areas in a series of malto-oligosaccharides and glucose, the wt. % of malto-oligosaccharides was calculated from the peak area ratio of glucose and malto-oligosaccharides. As a result, glucose was 24 wt. % and malto-oligosaccharides was 47 wt. % totaling to 71 wt. %, which agreed very well with the result of Example 3.

This analysis by HPLC took about 25 minutes for measuring one actual sample.

The results at this time are shown in Table 2, together with the results of Example 3.

TABLE 2

|  | Glucose (%) | Malto-oligosaccarides (%) | Total (%) |
| --- | --- | --- | --- |
| Example 3 | 24.8 | 46.8 | 71.6 |
| Drying method | — | — | 71.8 |
| HPLC | 24 | 47 | 71 |

In Table 2, the % unit shows the wt. %.

Thus, by using the apparatus shown in FIG. 8, the concentration of glucose and malto-oligosasccharides can be promptly and accurately measured at the same time.

This invention may be embodied in many other forms without departing from the true spirit or principal features thereof. It should be therefore understood that the foregoing embodiments are mere illustrative examples in every respect, and the scope of the invention is as described in the claims of the patent and is not limited whatsoever by the description in the specification herein.

It must be also noted that all changes and modifications belonging to the equivalent range of the scope of the claims fall within the scope of the invention.

What is claimed is:

1. An enzyme electrode for measuring malto-oligosaccharides, comprising an immobilized enzyme membrane containing glucoamylase and glucose oxidase, said glucoamylase and glucose oxidase being coimmobilized by a crosslinking agent in a single layer, wherein said glucoamylase and glucose oxidase are immobilized so that the ratio $$\frac{V_a}{V_o}$$

is $$12 \geq \frac{V_a}{V_o} \geq 0.4,$$

wherein $V_a$ is the maximum reaction rate of glucoamylase as expressed in the glucose formation rate from maltose and $V_o$ is the maximum reaction rate of glucose oxidase as expressed in the hydrogen peroxide formation rate from glucose.

2. An enzyme electrode for measuring malto-oligosaccharides claimed in claim 1, wherein the glucoamylase is derived from Rhizopus.

3. An enzyme electrode for measuring malto-oligosaccharides claimed in claim 1, wherein the glucoamylase is derived from Aspergillus.

4. An enzyme electrode for measuring malto-oligosaccharides claimed in claim 1, wherein the ratio $V_a/V_o$ is in a range of 1-10.

* * * * *